Nov. 27, 1962 E. B. LE GRICE Plant Pat. 2,197
ROSA FLORIBUNDA PLANT
Filed Aug. 15, 1961
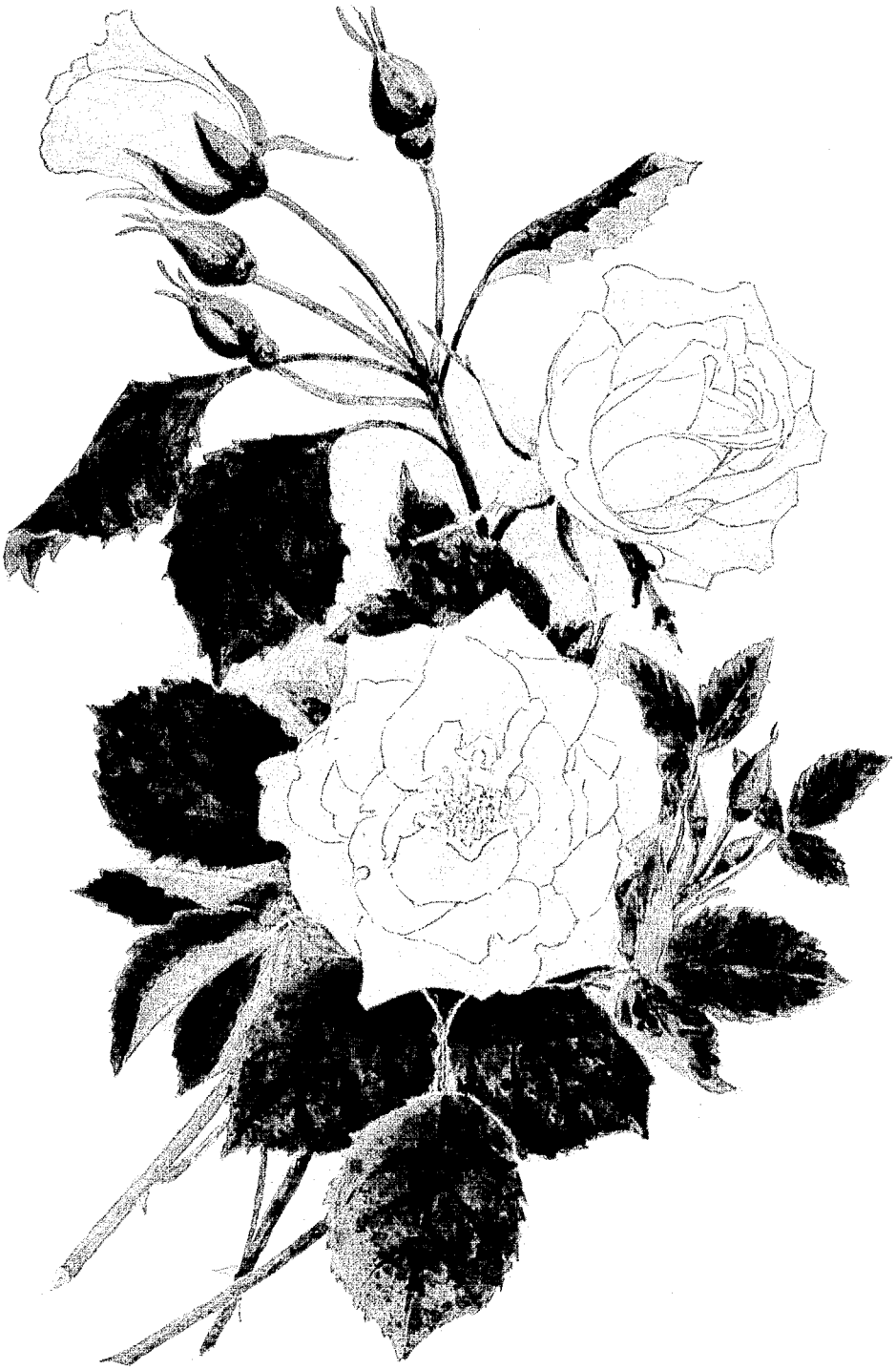
WITNESS
Addison T. Avery
INVENTOR
Edward Burton Le Grice,
by: John H. Leonard,
his ATTY.

United States Patent Office

Plant Pat. 2,197
Patented Nov. 27, 1962

2,197
ROSA FLORIBUNDA PLANT
Edward Burton Le Grice, North Walsham, Norfolk, England
Filed Aug. 15, 1961, Ser. No. 131,693
1 Claim. (Cl. 47—61)

This invention relates to a new variety of floribunda rose plant.

The present rose plant was produced originally by the crossing of an unnamed seedling, as a seed parent, and Marcel Bourgouin (Gallica), as the pollen parent.

The unnamed seedling is a cross of another unnamed seedling and Lavender Pinocchio, Plant Patent No. 947.

The new variety was crossed intentionally in my hybridizing greenhouse in North Walsham, England, in 1956.

The new variety has been asexually reproduced by me in 1957 at North Walsham, England, by budding.

The drawing shows in color a number of typical stalks with leaves, buds, blooms and thorns.

The roots are average with good winter resistance, when protected, and slight resistance unprotected. It has withstood winter temperatures down to 15° F.

The exposed portion of the plant is in the form of a hardy, perennial, woody bush which is upright, bushy, symmetrical in shape, and peaked at the top. A two year old plant grows generally to a height of about 2½ to 3 feet. It is a medium tall grower.

The exposed portion of the plant has good resistance to low temperatures when protected and fair resistance when unprotected. Its resistance to drought and wet seasons is good.

For growth, it prefers moderate sun or partial shade, with a west exposure. It thrives in well drained, rich loam soil.

The main stalks of the plant are upright, slightly branched and stiff. They are adequate to support the foliage and blooms well.

The following color designations are from the British Color Council Horticultural Color Chart and are designated by sheet and number.

The new growth of the stalks is Lettuce Green, No. 861/3. The old growth is Willow Green, No. 000862. The color is uniform.

The main stalks range from about 12 to 24 inches in length and are divergent. They have a smooth bark with few thorns. The branches are alternate. They are long and stiff, slightly curving, and adequate to support the foliage well.

The foliage in general is open, the leaf arrangement being alternate. The leaves are medium in quantity. The new leaves are Erythrite Red, No. 0027, on the top and No. 0027/2 on the bottom surfaces. The old leaves are Spinach Green, No. 0960 on the top and No. 0960/3 on the bottom. In the new leaves, the color is variegated, increasing in Spinach Green, showing first in veins and increasing in green area toward the base. The mature leaves are variegated, having a slight line of Erythrite Red.

The leaves are of average size, ranging from 4 inches average to 5½ inches maximum in length, and having a minimum width of about 4 inches and maximum of about 5 inches. The leaflets are of normal shape, or slightly broader than usual, being imparipinnate with serrated margins, hastate bases, and acuminate apices. They are of average thickness. They are smooth on the upper face and on the reverse. Their persistency on the plant is excellent and their leaf characteristics are normal.

The petioles or leaf stems are Spinach Green, No. 0960/3. They are average in length, being about 1 to 1¼ inches in length and strong. They have a smooth surface texture.

The stipules are slight.

The plant grows and blooms well in all temperate regions. It prefers sun, western exposures, dry seasons, and a well drained, neutral, rich loam soil. The blooms increase in number under optimum growing conditions, and are about 4½ inches in diameter. Under heat they are smaller and paler.

The plant blooms continuously for a period of about five months during June through October. The flowers remain in good condition for a long period when cut. The uncut flowers do not change color upon opening.

The buds are usual, being medium in size and plump. They are smooth and supported upright on terminals.

When the sepals first divide, the petal color is Spanish Orange, No. 010/1. When the petals begin to unfurl, the color is Spanish Orange, No. 010/3. When half blown, the color is Yellow Ochre, No. 07/3, the inner petals being slightly Salmon shade, No. 412/1. The outer side of the petals is veined Naples Yellow, No. 403.

The sepals are normal in shape and size.

The calyx is of normal shape and size with a normal surface texture.

The peduncles average from 2 to 4 inches in length. They are usual in texture and their color is Lettuce Green, No. 861/3 shaded to Erythrite Red, No. 0027. They are of average strength.

The pedicles average from 3 to 5 inches in length. Their texture is smooth and the color generally is Lettuce Green, No. 861/3, shaded slightly with Erythrite Red, No. 0027.

The blooms open slowly, the opening being hastened by heat. They average from 3½ inches in diameter to 4 inches in diameter, and an average plant will bear from 12 to 15 blooms at the same time. The blooms are borne in umbels. Each flower lasts about 5 days on the plant, and 4 days when cut.

Each bloom has from 23 to 30 petals. At the center of the bloom, the petals are Spanish Orange, No. 010/3. The outer petals are Yellow Ochre, No. 07/3. The base of the petals is Aureolin, No. 3 to Yellow Ochre, No. 07/3, on the inside. The reverse of the petals is a Yellow Ochre, No. 07/3, shaded with Salmon, No. 412/1.

The general tonality of the plant from a distance, when it is in bloom, is Egyptian Buff, No. 407. The color of the flower fades from Yellow Ochre, No. 07/3, to Egyptian Buff, No. 407/3.

The petals are thick and smooth and are glistening on the inside and dull on the outside. The outer petals are slightly recurvent. The arrangement of the petals is usual, and not imbricated. There are from 2 to 5 petaloids in the center and their persistence is good when cut or uncut.

The fragrance of the blooms is a strong, sweet and fruity perfume. Its lasting quality is good when the blooms are cut or uncut.

The stamens are normal Aureolin, No. 3, edged with Spanish Orange, No. 010/1 to 010/3. The filaments are medium. The pollen is Yellow Ochre, No. 07.

The styles are about ⅛ of an inch in length and are Erythrite Red, No. 0027. The stigmas are small and their color is Egyptian Buff, No. 407. The ovaries are plentiful. The fruit is normal.

There are few thorns on all stalks. They are short and of normal shape. Their color is Erythrite Red, No. 0027/3. They are unevenly distributed on the main stalk and on the laterals. There are none on the peduncles.

The drawing further illustrated the characteristics of the variety and the following tabulation is a detailed description of the new variety:

*General*

Parentage:

*Seed parent.*—Unnamed seedling. It is from a crossing of an unnamed seedling and Lavender Pinocchio, Plant Patent No. 947.

*Pollen parent.*—Marcel Bourgouin (gallica).

Classification: Botanic—Rosa Floribunda.

Blooming Habit: Location where observations were made—North Walsham, England, and Mentor, Ohio, U.S.A.

Bud:

*Size.*—Plump.

*Form.*—Usual.

*Color.*—When petals first divide, their color is Spanish Orange, No. 010/1. When they begin to unfurl, they are Spanish Orange, No. 010/3. When half blown, they are Yellow Ochre, No. 07/3, shaded to Salmon, No. 412/1, on the outer side and veined Naples Yellow, No. 403.

*Sepals.*—Normal shape and size.

*Calyx.*—Of the normal shape and size, with a normal surface texture.

*Peduncle.*—Length from 2 to 4 inches. Aspect—usual. Color—Lettuce Green, No. 861/3 shaded to Erythrite Red, No. 0027.

*Pedicles.*—Length 3 to 5 inches. Texture—smooth. Color—Lettuce Green, No. 861/3, shaded to Red, No. 0027.

*Opening.*—Slow—more quickly in hot sun.

Bloom:

*Size.*—3½ to 4½ inches in diameter. Average bloom per plant—12 to 15.

*Borne.*—Umbels.

*Stems.*—Length — about 3 inches to 5 inches. Strength—average. Aspect—smooth.

*Form.*—Usual.

*Permanence.*—5 days uncut; 4 days when cut.

Petalage:

*Texture.*—Thick and smooth.

*Appearance.*—Glistening on the inside and dull on the outside.

*Form.*—Usual.

*Arrangement.*—Usual, even outline, petals a little short.

*Petaloids.*—2 to 5.

*Persistence.*—Good, when cut and uncut.

*Fragrance.*—Outstanding, strong, sweet, and fruity.

*Lasting quality.*—Good when cut or uncut.

Genital organs:

*Stamens.*—Normal.

*Color.*—Aureolin, No. 3, edged with Spanish Orange. No. 010/1.

*Filaments.*—Medium.

*Pollen.*—Yellow Ochre, No. 07.

*Styles.*—Short. Color—Erythrite Red, No. 0027.

*Stigmas.*—Small, Egyptian Buff, No. 407.

*Ovaries.*—Plentiful.

*Plant*

Form: A hardy perennial woody bush, upright, bushy, and symmetrical in shape and peaked at top.

Growth: Medium. Height about 2½ feet to 3 feet for a two year old plant.

Foliage: Open.

*Leaf size.*—4 to 5½ in length and width of 3½ to five inches.

*Quantity.*—Medium.

*Color.*—New leaves on top—Erythrite Red, No. 0027. New leaves on bottom—Erythrite Red, No. 0027/2. Old leaves on top—Spinach Green, No. 0960/2. Old leaves on bottom—Spinach Green, No. 0960/3. Red foliage in young state, Erythrite Red, No. 0027.

*Shape.*—Imparipinnate with serrated margins, hastate bases, and acuminate apices.

*Texture.*—Upper surface — smooth. Lower face—smooth.

*Persistency*—Excellent.

*Leaf characteristics.*—Normal.

Petiole: Length—about 1¼ inches with a smooth surface texture. Strong. Color—Spinach Green, No. 0960/3.

Stipules: Slight.

Wood:

*Newest wood.*—Lettuce Green, No. 861/3.

*Bark.*—Smooth.

*Old wood.*—Willow Green, No. 000862.

Thorns:

*Quantity.*—On main stalks—few. Laterals—few.

*Form.*—Usual, except short.

*Color.*—Erythrite Red, No. 0027/3.

*Position.*—Unevenly distributed on main stalks and laterals and none on peduncles.

The plant is characterized particularly by the color of the blooms and the strong perfume.

Having shown and described my new variety of Rosa Floribunda plant and its manner of asexual reproduction, I claim;

The new and distinct variety of Rosa Floribunda plant herein shown and described.

No references cited.